United States Patent [19]

Gebert et al.

[11] 4,404,384
[45] Sep. 13, 1983

[54] O-[3-(4-SUBSTITUTED-PIPERAZIN-1-YL)-2-HYDROXYPROPYL]-HYDROXYLAMINES

[75] Inventors: Ulrich Gebert, Kelkheim; Werner Thorwart, Wiesbaden; Jaromir Komarek, Wiesbaden; Carl Cartheuser, Wiesbaden, all of Fed. Rep. of Germany

[73] Assignee: Hoechst Aktiengesellschaft, Frankfurt am Main, Fed. Rep. of Germany

[21] Appl. No.: 267,722

[22] Filed: May 28, 1981

Related U.S. Application Data

[63] Continuation of Ser. No. 121,910, Feb. 15, 1980, abandoned, which is a continuation of Ser. No. 850,057, Nov. 9, 1977, abandoned.

[30] Foreign Application Priority Data

Nov. 9, 1977 [DE] Fed. Rep. of Germany ....... 2651083

[51] Int. Cl.³ .................... C07D 295/08; A61K 31/50
[52] U.S. Cl. ................................ 544/394; 260/239 B; 424/250; 424/253; 424/256; 424/273 R; 424/274; 544/162; 544/277; 544/398; 546/264; 548/268; 548/333; 548/550; 564/301; 564/305; 564/306; 564/355
[58] Field of Search .............................. 544/394, 398

[56] References Cited

U.S. PATENT DOCUMENTS 4,358,450 11/1982 Gebert et al. ....................... 544/394

Primary Examiner—A. H. Sutto
Attorney, Agent, or Firm—Quaintance & Murphy

[57] ABSTRACT

A compound of general formula

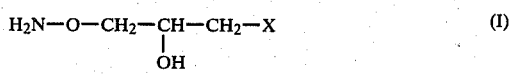

wherein X represents a radical selected from the group consisting of one of the formulae

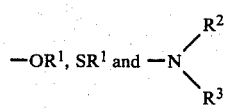

in which $R^1$ represents a radical selected from the group
 (a) a hydrogen atom,
 (b) an amino group, when X represents an —$OR^1$ moiety,
 (c) an alkyl group having from 1 to 6 carbon atoms
 (d) an at most binuclear aryl group being unsubstituted or substituted by at most 3 substituents of the group halogen atoms, alkyl, alkoxy, halogenalkyl groups each having up to 4 carbon atoms, cycloalkyl groups having 3 to 6 carbon atoms, nitro and cyano groups; and
$R^2$ and $R^3$, which may be the same or different, each represents a radical selected from the group
 (a) a hydrogen atom,
 (b) an alkyl group having from 1 to 6 carbon atoms, an unsubstituted cycloalkyl group having from 3 to 7 carbon atoms, such cycloalkyl group substituted by at most 3 substituents of the group hydroxy groups and alkoxycarbonyl groups having 1 to 4 carbon atoms,
 (c) an aralkyl group, a diaralkyl group each having 1 to 4 carbon atoms in the alkyl moiety and being unsubstituted or substituted in at least one of the radicals in the alkyl moiety by hydroxy groups, and in the aryl moieties by at most 3 substituents selected from the group consisting of alkoxy groups having from 1 to 4 carbon atoms and halogen atoms,
 (d) an at most binuclear aryl group being unsubstituted or substituted by at most 3 substituents selected from the group consisting of alkyl, alkoxy, halogenoalkyl groups each having up to 4 carbon atoms and halogen atoms,
 (e) a hydroxy group when the other of $R^2$ and $R^3$ is hydrogen,
 (f) $R^2$ and $R^3$, together with the nitrogen atom to which they are attached, represent a 5- to 7-membered ring selected from the group consisting of an unsubstituted ring, a ring being substituted by an alkyl group having from 1 to 4 carbon atoms, and a ring being interrupted by a heteroatom selected from the group consisting of oxygen, sulphur and further nitrogen atom, and
 (g) $R^2$ and $R^3$ together with the nitrogen atom to which they are attached, represent a ring from the group a 5-membered heteroaromatic ring containing up to 4 nitrogen atoms and such a ring being anelled to a benzene- or uracil-ring,
and physiologically acceptable acid addition salts thereof, a process for their preparation and a pharmaceutical composition containing them.

6 Claims, No Drawings

O-[3-(4-SUBSTITUTED-PIPERAZIN-1-YL)-2-HYDROXYPROPYL]-HYDROXYLAMINES

This application is a continuation of application Ser. No. 121,910, filed on Feb. 15, 1980, which is a continuation of application Ser. No. 850,057 filed on Nov. 9, 1977, both now abandoned.

This invention relates to O-alkylhydroxylamines having interesting pharmacological properties.

Many hydroxylamine derivatives, some having valuable biological properties, are known. Thus, for example, the preparation has been reported of some O-(2-hydroxyalkyl)-hydroxylamines, without further functional groups in the alkyl radical, by the N-hydroxyurethane method of E. Testa et al. [Helv.Chim.Acta 45, 358,1381 (1962)] and the N-hydroxyphthalimide method of W. Kliegel [Pharmazie 25, 400, 525 (1970)].

According to one aspect of the present invention there are provided compounds of general formula

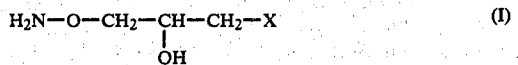

[wherein X represents a group of the formula

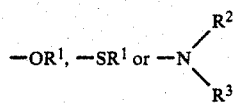

(in which $R^1$ represents
(a) a hydrogen atom,
(b) an amino group, when X represents an —$OR^1$ moiety,
(c) an alkyl group having from 1 to 6 carbon atoms or
(d) a mono- or binuclear aryl group optionally substituted by one or more halogen atoms or alkyl, alkoxy, halogenoalkyl groups each having up to 4 carbon atoms, cycloalkyl groups having 3 to 6 carbon atoms, nitro or cyano groups; and $R^2$ and $R^3$, which may be the same or different, each represents
(a) a hydrogen atom,
(b) an alkyl group having from 1 to 6 carbon atoms or cycloalkyl group having from 3 to 7 carbon atoms and optionally substituted by one or more hydroxy groups or alkoxycarbonyl groups having 1 to 4 carbon atoms,
(c) an aralkyl or diaralkyl group having 1 to 4 carbon atoms in the alkyl moiety and being optionally substituted in the alkyl moiety by hydroxy groups, and optionally substituted in the aryl moieties by one or more alkoxy groups having from 1 to 4 carbon atoms or halogen atoms,
(d) a mono- or binuclear aryl group optionally substituted by one or more alkyl, alkoxy or halogenoalkyl groups each having up to 4 carbon atoms or halogen atoms,
(e) a hydroxy group when the other of $R^2$ and $R^3$ is hydrogen, or
(f) $R^2$ and $R^3$, together with the nitrogen atom to which they are attached, represent a 5- to 7-membered saturated ring optionally substituted by an alkyl group having from 1 to 4 carbon atoms, and the ring being optionally interrupted by an oxygen, sulphur or further nitrogen atom or,
(g) $R^2$ and $R^3$ together with the nitrogen atom to which they are attached, represents a 5-membered heteroaromatic ring containing up to 4 nitrogen atoms and being optionally formed with a benzene- or uracil-ring)]
and physiologically acceptable acid addition salts thereof.

In the compounds according to the invention, alkyl radicals in $R^1$, $R^2$ and $R^3$ may be straight-chained or branched. In the compounds of general formula I, $R^2$ and $R^3$ together with the nitrogen atom to which are attached, preferably form a 5- to 7-member ring having a further heteroatom which is nitrogen substituted by an alkyl or hydroxyalkyl group each having up to 4 carbon atoms; an aralkyl or diarylalkyl group each having up to 4 carbon atoms in the alkyl moiety and the mono- or binuclear aryl radicals thereof are optionally substituted by halogen atoms; a mono- or binuclear aryl group optionally substituted by at least one alkyl, alkoxy, or halogenoalkyl group each having up to 4 carbon atoms, halogen atoms, hydroxy groups, or by a 3-aminooxy-2-hydroxypropyl group.

Aryl groups in any of $R^1$, $R^2$ and $R^3$ of the compounds according to the invention including the aryl substituents at the second N-atom of the saturated ring (f) may be substituted one or more times, for example, up to three times. When $R^2$ and $R^3$ take the values given under (b) and (c) above, the hydroxyl is preferably separated from a nitrogen atom in the group X, by 2 carbon atoms. An example of a binuclear aryl radical is the naphthalene system.

When $R^1$, $R^2$ and/or $R^3$ contain halogenoalkyl groups, these preferably contain 1 or 2 carbon atoms.

The compounds according to the invention exhibit interesting pharmacological properties. Depending on the nature of the substituent X they show blood-pressure-reducing, bronchospasmolytic, anti-convulsive, analgesic, antiphlogistic, choleretic, uric acid-reducing, anthelminthic and antifungal activity. They may also be useful as starting substances for the synthesis of other pharmacologically active compounds, such as, for example, for the preparation of substituted O-(2-hydroxypropyl)-aldoximes from 2-formyl-5-nitroimidazoles or 2-formyl-5-nitrofuran, as described in our copending patent Application No. of the same date (corresponding to German Patent Application P No. 26 51 084.9).

Preferred compounds according to the invention by reason of their favourable pharmacological properties are:
O-(3-phenoxy-2-hydroxypropyl)-hydroxylamine;
O-[3-(p-chlorophenoxy)-2-hydroxypropyl]-hydroxylamine;
O-[3-(2,4-dichlorophenoxy)-2-hydroxypropyl]-hydroxylamine;
O-[3-(3-methylphenoxy)-2-hydroxypropyl]-hydroxylamine;
O-[3-(4-methoxyphenoxy)-2-hydroxypropyl]-hydroxylamine;
O-[3-(4-cyanophenoxy)-2-hydroxypropyl]-hydroxylamine
O[3-(3-trifluoromethylanilino)-2-hydroxypropyl]-hydroxylamine;

O-[3-(4-diphenylmethyl-piperazin-1-yl)-2-hydroxy-propyl]-hydroxylamine and physiologically acceptable acid addition salts thereof.

According to further aspects of the present invention there are provided the following processes for the preparation of compounds of general formula I:

(a) reacting a hydroximic acid ester of formula

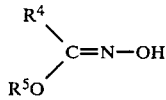  (II)

with a compound of formula

Y-CH$_2$-R$^6$  (III)

or reacting an O-alkylated hydroxylamine derivative of formula

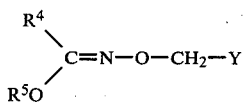  (IV)

with a compound of formula

HR$^6$  (V)

in each case to form a common intermediate compound of formula

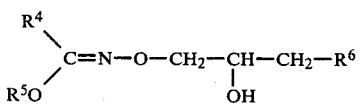  (VI)

and subsequently removing the protecting group of formula

to form a compound of formula I.

In the above formulae:

R$^4$ represents a straight-chained or branched alkyl group having from 1 to 6 carbon atoms or a mono- or binuclear aryl group optionally substituted by one or more alkyl or alkoxy groups having up to 2 carbon atoms or halogen atoms;

R$^5$ represents a straight-chained or branched alkyl group having from 1 to 6 carbon atoms;

R$^6$ is as hereinbefore defined for X or represents a group of the formula

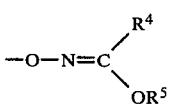

(in which R$^4$ and R$^5$ are as hereinbefore defined);

Y represents a group of the formula

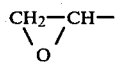

or

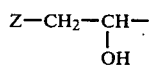

(in which

Z represents a halogen, preferably chlorine or bromine atom, or a reactive sulphonic acid ester group).

The protecting group is preferably removed hydrolytically as a compound of formula R$^4$COOR$^5$.

If in the above processes the compounds of general formula I are produced as their free bases they may, if desired, be converted with suitable acids into the corresponding physiologically compatible acid addition salts in known manner.

In the synthesis of compounds of general formula I according to the above processes in which X represents the group —O—NH$_2$, an intermediate compound protected on both sides having the formula

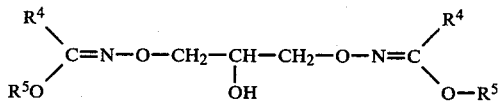  (VII)

(wherein R$^4$ and R$^5$ are as hereinbefore defined) may be obtained when using a compound of formula III or V in which R$^6$ represents an

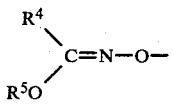

group.

Especially useful compounds of formula II are alkyl esters having from 1 to 4, and preferably 1 or 2 carbon atoms in the alkoxy group, such as, for example, methyl benzohydroximate and advantageously ethyl acetohydroximate. Such compounds can be readily prepared according to processes known per se from the corresponding imido esters and hydroxylamine [see for example, J. Houben and E. Schmidt, Ber. dt. Chem. Ges. 46 3619 (1913)].

Starting compounds of general formula III are preferably 2,3-epoxypropyl derivatives which are generally known per se or can easily be prepared by processes known to those skilled in the art, for example, from epihalogenhydrins, especially epichlorohydrin, and nucleophilic compounds of general formula V in the presence of a base. The 2-propanols of formula III

Z-CH$_2$-CH(OH)-CH$_2$-X (wherein X and Z are as hereinbefore defined) are similarly suitable as starting compounds and can be prepared, in principle, in the same way, but with the exclusion of basic condensation agents, from epoxides such as epichlorohydrin, epibromohydrin and 2,3-epoxypropylbenzenesulphonate, toluenesulphonate, 4-bromo-benzenesulphonate or methanesulphonate.

The preferred process for the preparation of compounds I according to the invention comprises reacting the novel O-(2,3-epoxypropyl)-hydroximic acid esters of formula IV described in our copending Patent Application No. of the same date (corresponding to German Patent Application P 26 51 085.0) with alcohols, thiols, phenols, thiophenols, amines or 5-membered aromatic nitrogen heterocycles of formula V according to alternative process b). In this case, the alkyl O-(2,3-epoxypropyl)-benzohydroximates or alkyl-O-(2,3-epoxypropyl)-acetohydroximates with 1 to 4, preferably 1 or 2 carbon atoms in the alkoxy group, e.g. methyl O-(2,3-epoxypropyl)-benzohydroximate and especially ethyl O-(2,3-epoxypropyl)-acetohydroximate, have proved particularly useful.

The amines of formula V which may with advantage be used are those saturated cyclic compounds which are unsubstituted or which carry up to 4 alkyl radicals, preferably pyrrolidine, 2,5-dimethylpyrrolidine, piperidine, 2,6-dimethylpiperidine, 2,2,6,6-tetramethylpiperidine, hexamethyleneimine or compounds which contain an oxygen, sulphur or further nitrogen atom in the heterocycle and which are preferably separated by at least 2 carbon atoms from the nitrogen atom of the

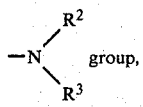

group, such as, for example, morpholine, thiamorpholine, tetrahydro-1,4-thiazin-1,1-dioxide, piperazine and homopiperazine, where the second nitrogen atom of the heterocycle, e.g. the 4-position of piperazine cycle can carry, instead of hydrogen, optionally substituents such as, for example, the substituents indicated in Examples 47 to 62. Convenient 5-membered, aromatic, optionally anelled nitrogen-heterocycles are pyrrole, indole, pyrazole, indazole, imidazole, benzimidazole, triazole, benzotriazole, tetrazole, carbazole and xanthines such as theophylline.

The alkylation reactions according to processes (a) and (b) are conveniently effected in a solvent or dispersion agent which in inert towards the reactants under the reaction conditions, advantageously at temperatures between 0° and 200° C., preferably between 50° C. and the boiling point of the reaction mixture, either in the presence of a base such as, for example, alkali metal or alkaline-earth metal hydroxides, carbonates, hydrides and alcoholates or organic bases such as triethylamine, pyridine, picoline and quinoline, or by use of alkali metal or alkaline-earth metal salts of the hydroximic acid esters of formula II or the alcohols, thiols, phenols, thiophenols and nitrogen heteroaromatic compounds of formula V. The reaction times may generally be from 1 hour to a few days.

Examples of solvents inert under the reaction conditions are, for example, anhydrous alcohols such as, for example, methanol, ethanol, propanol, isopropanol, butanol or isobutanol; ethers such as diethyl ether, diisopropyl ether, tetrahydrofuran, dioxane or diethyleneglycoldimethyl ether; hydrocarbons such as hexane, cyclohexane, petroleum ether, benzene, toluene or xylene; halogenated hydrocarbons such as dichloromethane, chloroform, carbon tetrachloride or chlorobenzene; aprotic solvents such as dimethylformamide, dimethylacetamide, N-methylpyrrolidone, tetramethylurea, hexamethylphosphoric acid trisamide, dimethylsulphoxide or acetonitrile; and, if desired mixtures of any of the above solvents.

Reaction of the hydroxylamine derivatives of formula II with epoxides of formula III according to process (a) and the addition of thiols, phenols, thiophenols or nitrogen aromatic heterocyclic compounds of formula V to the oxiranes of formula IV according to process (b), are preferably effected in dimethylformamide with the addition of triethylamine as catalyst at temperatures between 50° and 100° C. The starting compounds are advantageously used in equimolar quantities or with a slight excess of the alkylating agent.

On the other hand, alkylation according to process (a) of a compound of formula II with the 2-propanols of formula III advantageously takes place using alkali metal or alkaline-earth metal hydroximates in alcoholic solution at reflux temperature.

Aminolysis of the oxiranes of formula IV with amines of formula V according to process (b) is preferably effected by refluxing for 1 to 5 hours in alcohols having a higher boiling point than methanol, such as, for example, n-propanol (b.p. 97° C.) or isopropanol (b.p. 82° C.) in the absence of a further base, in which case primary amines are preferably present in an excess of up to 4 times the stoichiometric quantity.

In general, purification of the pure intermediate compounds of formula VI and VII obtained by the processes (a) or (b) is not necessary for subsequent hydrolytic removal of the protecting group. If desired, however, purification may be effected by fractional distillation under reduced pressure or, in some cases by crystallization. Some intermediate compounds of formula VI thus isolated and analytically characterized are given in Table 3. Hydrolytic splitting of the protecting group from the intermediate is preferably carried out under acid conditions in aqueous, aqueous alcoholic or aqueous ether solution at temperatures from 0° to 120° C., advantageously from 60° to 110° C., the reaction time is usually between a few minutes and a few hours. Especially suitable for this reaction are dilute mineral acids such as hydrochloric acid and sulphuric acid. The O-alkylated hydroximic acid esters of formula VI are advantageous in that their protecting group can be separated as carboxylic acid esters of formula I $R^4$-COO$R^5$ quickly, gently and quantitatively under particularly mild reaction conditions.

As indicated above the products of the process according to the invention may be isolated either in the form of stable free bases or preferably as non-toxic acid addition salts. Suitable acids for the preparation of acid addition salts are, for example, halogen hydracids (such as hydrobromic acid and especially hydrochloric acid), sulphuric, phosphoric, acetic, lactic, maleic, fumaric, oxalic, tartaric, citric, gluconic, p-toluenesulphonic, methanesulphonic, benzenesulphonic and cyclohexylamido sulphonic acid.

It will be appreciated that the compounds of formula I according to the invention have a chiral carbon atom and can thus exist as racemates or as optically active D or L isomers. All such forms are intended to be within the scope of the present invention.

In order to produce the individual optical isomers of the compounds of general formula I, processes (a) and (b) may be effected using enantiomeric starting compounds of formula III or IV or racemates obtained by these processes may be resolved into the optical isomers by means of processes known per se, e.g. by fractional crystallisation of the acid addition salts obtained from optically active acids.

As indicated above the compounds of general formula I according to the invention exhibit interesting pharmacological properties.

Thus, according to a further aspect of the present invention there are provided pharmaceutical compositions comprising as active ingredient at least one compound of general formula I or a physiologically acceptable acid addition salt thereof in combination with a pharmaceutical carrier or excipient.

The compositions according to the invention may be conveniently administered orally or parenterally. Suitable solid or liquid forms of administration are, for example, granules, powders, tablets, capsules, syrups, emulsions, suspensions, drops or injectible solutions and forms adapted to provide a sustained release of active ingredient(s). Convenient carriers for use in the compositions of the invention are e.g. magnesium carbonate, various sugars, starch, cellulose derivatives, gelatine, animal and vegetable oils, polyethylene glycols, solvents and excipients conventionally used in the pharmaceutical art.

The compositions according to the invention may, if desired, additionally comprise further pharmacologically active ingredients such as, for example, diuretics, saluretics, α- and especially β-sympatholytics, tranquillisers, blood-vessel-dilating agents and anti-hypertensives.

Pharmacological Tests

The effect on blood-pressure of compounds of general formula I according to the invention has been investigated in animal experiments using normotonic bastard dogs of both sexes under sodium pentobarbital anaesthesia (35–40 mg/kg i.p.).

During the tests the animals were laid on an operating table heated to 37° C. and breathed spontaneously through a tracheal tube. To prevent blood coagulation they received 2 mg/kg of heparin i.v.

The compounds tests were administered
(a) intravenously (i.v.) in aqueous solution through a polyvinyl chloride catheter into the femoral vein. The administration time was in each case 30 seconds; or
(b) intraduodenally (i.d.) in the form of carboxymethyl cellulose suspensions through a polyvinyl chloride catheter into the duodenum.

The following cardio-vascular parameters were measured:
1. p=average arterial blood pressure measured in mmHg through a polyvinyl chloride catheter using a Statham electronic pressure pick-up,
2. heart frequency (min$^{-1}$) measured by an ECG (electrocardiogram) (II, extremity derivation) by counting the R peaks, and
3. dp/dt$_{max}$ (mmHg. sec$^{-1}$) by means of a differentiator.

The most important test results are summarised in Table 1.

For comparison, the commercially available antihypertensive, prazosin, (1-(4-amino-6,7-dimethoxy-2-ehinazolinyl)-4-(2-furoyl)-piperazine hydrochloride) was used. With this compound blood-pressure reduction is generally accompanied by an undesirable tachycardia. In contrast, the compounds according to the invention which we have tested generally show a bradycardiac action and therefore relieve the heart. The pressor reaction to catecholamines delivered exogenically is only inhibited moderately by the compounds while the comparison compound provokes a complete blockage of the α-receptors which gives rise to a reversal of the adrenalin reaction.

Thus, the compounds of formula I tested have shown no α-sympathicolytic activity on the isolated seminal vesicle of the guinea pig, whereas prazosin has a strong α-sympathicolytic activity comparable to phentolamine.

In the following table n means the number of tested animals.

TABLE 1

| | | | | Blood-pressure-reducing activity | |
|---|---|---|---|---|---|
| Compound of Example | Dose in mg/kg | Route of application | n | maximum reduction of average arterial blood pressure in % | Interval till starting value of blood pressure is regained in Min. |
| 2 | 30 | i.d. | 2 | −27 | 63 |
| | 50 | | 2 | −32 | 52 |
| 10 | 3 | i.v. | 3 | −11 | 8 |
| | 6 | | 3 | −16 | 14 |
| | 20 | i.d. | 4 | −19 | 37 |
| | 30 | | 2 | −24 | >100 |
| | 50 | | 6 | −37 | >55 |
| 12 | 20 | i.d. | 2 | −18 | 66 |
| | 50 | | 2 | −43 | 118 |
| 13 | 3 | i.v. | 2 | −14 | 9 |
| | 6 | | 2 | −19 | 16 |
| | 20 | i.d. | 2 | −18 | 70 |
| | 50 | | 2 | −33 | >45 |
| 15 | 3 | i.v. | 2 | −28 | 7 |
| | 6 | | 2 | −33 | 20 |
| | 20 | i.d. | 2 | −25 | 36 |
| | 50 | | 2 | −34 | 68 |
| 19 | 3 | i.v. | 2 | −15 | 5 |
| | 6 | | 2 | −20 | 16 |
| | 10 | i.d. | 1 | −31 | >110 |
| | 20 | | 1 | −37 | >120 |
| | 30 | | 1 | −50 | 85 |
| | 50 | | 2 | −48 | >100 |
| 39 | 6 | i.v. | 2 | −30 | 33 |
| 50 | 6 | i.v. | 2 | −52 | 40 |
| 53 | 3 | i.v. | 2 | −40 | 55 |
| | 6 | | 2 | −45 | >45 |
| | 20 | i.d. | 2 | −38 | 170 |
| | 50 | | 2 | −41 | 178 |
| 54 | 3 | i.v. | 3 | −42 | >75 |
| | 6 | | 2 | −42 | >70 |
| 56 | 6 | i.v. | 2 | −48 | >115 |
| | 20 | i.d. | 2 | −45 | >220 |
| 58 | 3 | i.v. | 1 | −47 | 65 |
| | 6 | | 1 | −52 | 150 |
| | 20 | i.d. | 2 | −40 | >200 |

The following Examples serve to illustrate the preparation of compounds of general formula I. The structure of the compounds described below has been proved by elemental analysis and by reference to i.r. and $^1$H-n.m.r. spectra.

EXAMPLE 1

(a) Ethyl-O-(2,3-dihydroxypropyl)-acetohydroximate (see formula VIII, Table 3) (According to process a) A solution of 23 g (1 gram atom) of metallic sodium in 500 ml of anhydrous ethanol at room temperature has added to it 103.1 g (1 mol) of ethyl acetohydroximate, the mixture is stirred for 30 minutes and then 188.8 g (1.7 mol) of 3-chloropropane-1,2-diol are added dropwise, the temperature rises to approximately 45° C. After heating for 3 hours with reflux the mixture is allowed to cool, filtered from the precipitated sodium chloride and the filtrate evaporated under reduced pressure. Fractional distillation under reduced pressure of the oily residue yields 114 g (64.5% of theory) of the title compound, boiling point (0.1 mm Hg) 34° C.

$C_7H_{15}NO_4$ (M.W. = 177.2).

(b) O-(2,3-Dihydroxypropyl)-hydroxylamine hydrochloride (see Table 2)

88.6 g (0.5 mol) of the ester produced by step (a) above are mixed with 500 ml of 2 N hydrochloric acid in order to remove the protecting group in the form of ethyl acetate, and heated for 15 minutes with reflux. After cooling, the solution is evaporated under reduced pressure and the solid residue is recrystallised from isopropanol, 67.1 g (93.4% of theory) of the title compound having a melting point of 87°–88° C. are obtained.

$C_3H_{10}ClNO_3$ (M.W. = 143.6).

Analysis: Calculated: C 25.10%, H 7.02%, Cl 24.69%, N 9.76%; Found: C 25.38%, H 7.20%, Cl 24.78%, N 9.55%.

EXAMPLE 2

(a)

Ethyl-O-(3-phenoxy-2-hydroxypropyl)-acetohydroximate (see formula IX, Table 3) (According to process a)
51.5 g (0.5 mol) of ethyl acetohydroximate are dissolved in 250 ml of dimethylformamide, 7 ml of triethylamine are added and mixed by stirring with 82.5 g (0.55 mol) of 1-phenoxy-2,3-epoxypropane. The reaction mixture is subsequently stirred for 48 hours at 50° C., a further 7.5 g (0.05 mol) of the epoxide being added after 24 hours. After distillation of the solvent under reduced pressure, fractional distillation of the oily residue under reduced pressure yields 108.5 g (85.7% of theory) of the title compound, boiling point (0.07 mm Hg) 127°–129° C., melting point 41°–43° C.; $\alpha_D^{20} = 1.5109$, $C_{13}H_{19}NO_4$ (M.W. = 253.3).

Analysis: Calculated: C 61.64%, H 7.56%, N 5.53%; Found: C 61.86%, H 7.60%, N 5.44%.

(b) O-(3-Phenoxy-2-hydroxypropyl)-hydroxylamine hydrochloride (see Table 2)

81.3 g (0.32 mol) of the ester prepared in step (a), are dispersed in 320 ml of 2 N hydrochloric acid and heated for 15 minutes with vigorous stirring and reflux, a clear solution is obtained which is evaporated to dryness after cooling under reduced pressure. Re-crystallisation of the crystalline crude product (70 g = 100% of theory) from ethanol with the addition of diethyl ether at boiling temperature until precipitation yields 66.8 g (95% of theory) of the title compound, which decomposes above 138° C. with the evolution of gas.

$C_9H_{14}ClNO_3$ (M.W. = 219.7).

Analysis: Calculated: C 49.21%, H 6.42%, Cl 16.14%, N 6.38%; Found: C 49.09%, H 6.24%, Cl 16.20%, N 6.46%.

EXAMPLE 3

O-[3-(3,4-Dichlorophenoxy)-2-hydroxypropyl]hydroxylamine hydrochloride (see Table 2) (According to process b)

A solution of 16.3 g (0.1 mol) of 3,4-dichlorophenol and 10.1 g (0.1 mol) of triethylamine in 100 ml of dimethylformamide is mixed with 15.9 g (0.1 mol) of ethyl O-(2,3-epoxypropyl)acetohydroximate and the reaction mixture is stirred for 40 hours at 95°–100° C. Afterwards, the solvent is distilled off under reduced pressure and the residue fractionally distilled under reduced pressure to give 26.2 g (81.3% of theory) of ethyl O-[3-(3,4-dichlorophenoxy)-2-hydroxypropyl]-acetohydroximate of boiling point (3 mm Hg) 178°–180° C. To give the hydroxylamine, the distillate (81.3 mmol) is heated in 100 ml of 2 N hydrochloric acid for 15 minutes with reflux, the cooled solution is evaporated to dryness under reduced pressure and the solid residue is recrystallised from ethanol.

Yield: 16.4 g (70% of theory); melting point: 152° C. (with decomposition). $C_9H_{12}Cl_3NO_3$ (M.W. = 288.6).

Analysis: Calculated: C 37.46%, H 4.19%, Cl 36.86%, N 4.85%; Found: C 37.43%, H 4.29%, Cl 36.42%, N 4.83%.

EXAMPLE 4

O-(3-Amino-2-hydroxypropyl)-hydroxylamine dihydrochloride (see Table 2) (According to process b)

15.9 g (0.1 mol) of ethyl O-(2,3-epoxypropyl)-acetohydroximate are dissolved in 165 ml of ethanol, mixed with 166 ml of an aqueous ammonia solution enriched with NH₃ gas (prepared by introducing NH₃ gas into 140 ml of 25% ammonia solution with ice cooling to a total volume of 166 ml) and shaken in a sealed pressure vessel for 17 hours at room temperature. Before the apparatus is opened the mixture is cooled to −30° C., the ammonia is allowed to partially escape at room temperature and the residue is evaporated together with a solvent under reduced pressure. The oily residue is mixed with 150 ml of 2 N hydrochloride acid to remove the protecting group and stirred for 15 minutes at boiling temperature. It is then allowed to cool, the excess acid is removed under reduced pressure and the solid residue is re-crystallised from ethanol with the addition of diethyl ether at boiling heat until precipitation.

Yield: 9.2 g (51.4% of theory); melting point 155°–156° C. (with decomposition).

$C_3H_{12}Cl_2N_2O_2$ (M.W. = 179.1).

Analysis: Calculated: C 20.13%, H 6.76%, Cl 39.60%, N 15.65%; Found: C 20.23%, H 6.87%, Cl 39.61%, N 15.66%.

The free base of this compound can be distilled off under reduced pressure without decomposition: boiling point (0.04 mm Hg) 100°–103° C.

EXAMPLE 5

O-[3-(4-morpholinyl)-2-hydroxypropyl]-hydroxylamine dihydrochloride (see Table 2) (According to alternative process b)

A solution of 79.6 g (0.5 mol) of ethyl O-(2,3-epoxypropyl)-acetohydroximate and 43.6 g (0.5 mol) of morpholine is heated in 300 ml of n-propanol for 4 hours with reflux. It is then allowed to cool, the alcohol is distilled off under reduced pressure, the residue mixed with 750 ml of 2 N hydrochloric acid and the mixture boiled for 15 minutes with vigorous stirring. The mixture is then evaporated under reduced pressure and the solid crude product is re-crystallised from methanol with the addition of diethyl ether at boiling heat until precipitation.

Yield: 112.7 g (90.5% of theory); melting point 178°–180° C. (with decomposition).

$C_7H_{18}Cl_2N_2O_3$ (M.W. = 249.1%).

Analysis: Calculated: C 33.75%, H 7.28%, Cl 28.46%, N 11.24%; Found: C 33.54%, H 7.46%, Cl 28.34%, N 11.04%.

The same compound may be obtained by analogous reaction of equimolar quantities of morpholine and methyl O-(2,3-epoxypropyl)-benzohydroximate with a yield of 98% of theory.

The free base of the dihydrochloride can be isolated in crystalline form. After re-crystallisation from diisopropyl ether it has a melting point of 80°–81° C.; $C_7H_{16}N_2O_3$ (M.W. = 176.2).

Analysis: Calculated: C 47.71%, H 9.15%, N 15.90%; Found: C 47.96%, H 9.35%, N 15.99%.

EXAMPLE 6

O-[3-(1-Imidazolyl)-2-hydroxypropyl]-hydroxylamine dihydrochloride (see Table 2) (According to process b)

Solution of 127.4 g (0.8 mol) of ethyl O-(2,3-epoxypropyl)acetohydroximate and 54.5 g (0.8 mol) of imidazole in 500 ml of dimethylformamide is mixed with 15 ml of triethylamine and the mixture is stirred for 35 hours at 80° C. The oil obtained after evaporation under reduced pressure is dissolved in 500 ml of 4 N hydrochloric acid and heated for 15 minutes with reflux. The mixture is subsequently evaporated to dryness under reduced pressure and the residue is re-crystallised from ethanol.

Yield: 129 g (70.1% of theory); melting point 132° C.; $C_6H_{13}Cl_2N_3O_2$ (M.W. = 230.1).

Analysis: Calculated: C 31.32%, H 5.70%, Cl 30.82% N 18.26%; Found: C 31.01%, H 5.92%, Cl 30.56%, N 18.04%.

EXAMPLE 7

1,3-bis-Amino-oxy-2-hydroxypropane dihydrochloride (see Table 2)

10.3 g (0.1 mol) of ethyl acetohydroximate is added to a solution of 2.3 g (0.1 gram atom) of sodium in 100 ml of anhydrous methanol at room temperature, the mixture is stirred for 30 minutes and the alcohol distilled off under reduced pressure. The sodium salt thus obtained is suspended in 100 ml of dry dioxan and mixed dropwise with 15.9 g (0.1 mol) of ethyl O-(2,3-epoxypropyl)-acetohydroximate with vigorous stirring. The mixture is then heated for 3 hours with reflux, the solvent is removed under reduced pressure, and the residue dissolved in water. The alkaline solution obtained is neutralised with 2 N hydrochloric acid and the 1,3-bis-(1-ethoxy-ethylideneamino-oxy)-2-hydroxypropane of formula (VII) ($R^4$=CH$_3$ and $R^5$=C$_2$H$_5$) is extracted with ethyl acetate. Evaporation of the organic phase under reduced pressure after drying over sodium sulphate, yields an oily residue which after dissolving in 100 ml of 2 N hydrochloric acid is boiled for 15 minutes with reflux. Removal of the solvent under reduced pressure and re-crystallisation of the solid residue from ethanol with the addition of diethyl ether at boiling temperature until turbidity yields 10 g (52% of theory) of the title compound having a melting point of 155°–156° C. $C_3H_{12}Cl_2N_2O_3$ (M.W. = 195.1).

Analysis: Calculated: C 18.47%, H 6.20%, Cl 36.35%, N 14.36%; Found: C 18.86%, H 6.48%, Cl 36.37%, N 14.07%.

The compounds listed in the following Table 2 may be prepared analogously according to processes (a) and/or (b):

TABLE 2

Examples according to formula

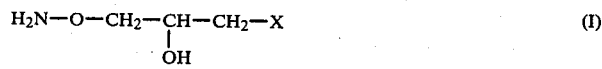

$$H_2N-O-CH_2-CH(OH)-CH_2-X \quad (I)$$

| Example | X | Process | isolated as | Melting or boiling point (mm Hg) °C. |
|---|---|---|---|---|
| 1 | OH— | a | 1 HCl | 87–88 |
| 2 | C₆H₅—O— | a | 1 HCl | 138 (decomp.) |
| 3 | 2,4-Cl₂-C₆H₃—O— | b | 1 HCl | 152 (decomp.) |
| 4 | H₂N— | b | 2 HCl | 155–156 (decomp.) |
| 5 | morpholin-4-yl— | b | 2 HCl / Base | 178–180 (decomp.) / 80–81 |
| 6 | 1-imidazolyl— | b | 2 HCl | 132 |

TABLE 2-continued
Examples according to formula $$H_2N-O-CH_2-CH(OH)-CH_2-X \quad (I)$$

| Example | X | Process | isolated as | Melting or boiling point (mm Hg) °C. |
|---|---|---|---|---|
| 7 | H$_2$N—O— | a/b | 2 HCl | 155–156 |
| 8 | CH$_3$—(CH$_2$)$_3$—O— | a | Base | 97–101 (0,2) |
| 9 | 1-naphthyl-O— | a | Base<br>1 HCl | 65–67 (decomp.)<br>193–194 (decomp.) |
| 10 | 4-Cl-C$_6$H$_4$-O— | a | 1 HCl | 170–172 |
| 11 | 2-Cl-C$_6$H$_4$-O— | a | 1 HCl | 154–155 |
| 12 | 2,4-Cl$_2$-C$_6$H$_3$-O— | a | 1 HCl | 160 |
| 13 | 3-CH$_3$-C$_6$H$_4$-O— | a | 1 HCl | 165–167 |
| 14 | 2-cyclohexyl-C$_6$H$_4$-O— | a | 1 HCl | 119–120 |
| 15 | 4-CH$_3$O-C$_6$H$_4$-O— | a | 1 HCl | 140–142 |
| 16 | 3,4,5-(CH$_3$O)$_3$-C$_6$H$_2$-O— | b | 1 HCl | 176 |
| 17 | 3-CF$_3$-C$_6$H$_4$-O— | b | 1 HCl | 159–160 (decomp.) |

TABLE 2-continued

Examples according to formula $$H_2N-O-CH_2-CH(OH)-CH_2-X \quad (I)$$

| Example | X | Process | isolated as | Melting or boiling point (mm Hg) °C. |
|---|---|---|---|---|
| 18 | 4-Br-C$_6$H$_4$-O- | a | 1 HCl | 178–179 |
| 19 | 4-HC≡C-C$_6$H$_4$-O- | a | 1 HCl | 167 |
| 20 | C$_6$H$_5$-S- | a | 1 HCl | 120–121 |
| 21 | -NH-C$_2$H$_5$ | b | Base | Oil |
| 22 | -N(C$_2$H$_5$)$_2$ | b | Base | 80 (0,3) |
| 23 | -N(CH$_2$-CH$_2$-CH$_2$-CH$_3$)$_2$ | b | 2 HCl | Oil |
| 24 | -NH-CH(CH$_3$)$_2$ | b | 2 HCl | 155–157 (decomp.) |
| 25 | -NH-C(CH$_3$)$_3$ | b | Base<br>2 HCl | 102 (0,5)<br>188 |
| 26 | -NH-C$_6$H$_{11}$ | b | Base | Oil |
| 27 | -N(CH$_2$-CH$_2$-OH)$_2$ | b | Base | 145 (0,5) |
| 28 | -NH-CH(CH$_3$)-C(=O)-OC$_2$H$_5$ | b | 2 HCl | strongly hygroscopic |
| 29 | -NH-CH(CH$_3$)-CH$_2$-C$_6$H$_5$ | b | 2 HCl | 141–142 (decomp.) |

TABLE 2-continued

Examples according to formula $$H_2N-O-CH_2-CH(OH)-CH_2-X \quad (I)$$

| Example | X | Process | isolated as | Melting or boiling point (mm Hg) °C. |
|---|---|---|---|---|
| 30 | −N(CH₃)−CH(CH₃)−CH(OH)−phenyl | b | 2 HCl × 1 C₂H₅OH | strongly hygroscopic |
| 31 | −NH−CH(phenyl)₂ | b | 2 HCl | 179–180 (decomp.) |
| 32 | −NH−CH₂−CH₂−C₆H₄−OCH₃ (4-) | b | 2 HCl | 157–158 (decomp.) |
| 33 | −NH−CH(phenyl)(4-Cl-phenyl) | b | 2 HCl | 185–186 (decomp.) |
| 34 | −NH−phenyl | b | 2 HCl | 168–170 (decomp.) |
| 35 | −N(CH₃)−phenyl | b | Base | 150 (0,3) Fp. 50° C. |
| 36 | −NH−(2,6-dimethylphenyl) | b | 2 HCl | 213–214 (decomp.) |
| 37 | −NH−(2,4,6-trimethylphenyl) | b | 2 HCl | 200 (decomp.) |

TABLE 2-continued

Examples according to formula $$H_2N-O-CH_2-\underset{\underset{OH}{|}}{CH}-CH_2-X \qquad (I)$$

| Example | X | Process | isolated as | Melting or boiling point (mm Hg) °C. |
|---|---|---|---|---|
| 38 | —NH—C₆H₄—OCH₃ (ortho) | b | 2 HCl | 175–176 (decomp.) |
| 39 | —NH—C₆H₄—CF₃ (meta) | b | 2 HCl | 175–176 (decomp.) |
| 40 | —NH—C₆H₄—Cl (para) | b | 2 HCl | 179–181 (decomp.) |
| 41 | —N(pyrrolidine) | b | 2 HCl | 154 (decomp.) |
| 42 | —N(piperidine) | b | 2 HCl | oil |
| 43 | —N(hexamethyleneimine) | b | Base<br>1 HCl | 110–112 (0,2)<br>92 |
| 44 | —N(2,5-dimethylpyrrolidine) | b | Base<br>1 HCl | 101 (0,03)<br>110–112 |
| 45 | —N(2,6-dimethylpiperidine) | b | Base<br>1 HCl | 120 (0,2)<br>138–140 |
| 46 | —N(2,2,6,6-tetramethylpiperidine) | b | 2 HCl | Oil |

TABLE 2-continued
Examples according to formula
$$H_2N-O-CH_2-CH(OH)-CH_2-X \quad (I)$$
| Example | X | Process | isolated as | Melting or boiling point (mm Hg) °C. |
|---|---|---|---|---|
| 47 | 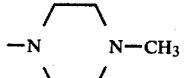 | b | 3 HCl | 187 (decomp.) |
| 48 | 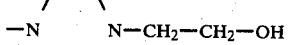 | b | 3 HCl × 1 H$_2$O | 115 |
| 49 | 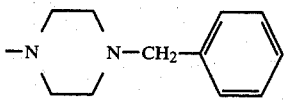 | b | 3 HCl | 184–185 (decomp.) |
| 50 | 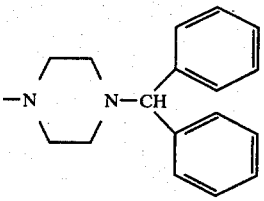 | b | fumarate 3 HCl | 182–183 from 168 (decomp.) |
| 51 | 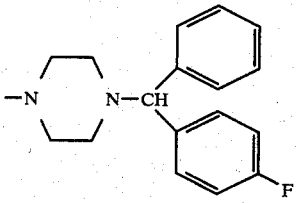 | b | 3 HCl | 166–168 (decomp.) |
| 52 | 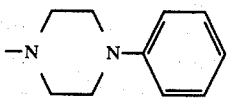 | b | 3 HCl | 178–179 (decomp.) |
| 53 | 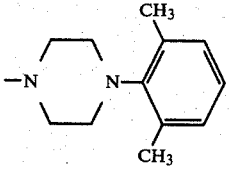 | b | 2 HCl | 152–154 |
| 54 | 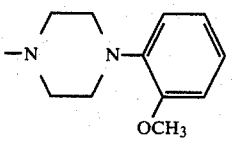 | b | 3 HCl × 1 H$_2$O | 142 (decomp.) |
| 55 | 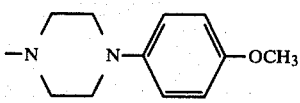 | b | 3 HCl | 153–155 (decomp.) |

TABLE 2-continued
Examples according to formula $$H_2N-O-CH_2-CH(OH)-CH_2-X \quad (I)$$

| Example | X | Process | isolated as | Melting or boiling point (mm Hg) °C. |
|---|---|---|---|---|
| 56 | -N(piperazinyl)-N-(2-ethoxyphenyl) [OC₂H₅] | b | 1 HCl | 153-154 (decomp.) |
| 57 | -N(piperazinyl)-N-(3-trifluoromethylphenyl) [CF₃] | b | 2 HCl | 197-198 |
| 58 | -N(piperazinyl)-N-(2-chlorophenyl) [Cl] | b | 2 HCl | 177-178 (decomp.) |
| 59 | -N(piperazinyl)-N-(4-hydroxyphenyl) [OH] | b | 3 HCl | 192-194 (decomp.) |
| 60 | -N(piperazinyl)-N-(2-hydroxyphenyl) [OH] | b | 3 HCl | 182-184 (decomp) |
| 61 | -N(piperazinyl)-N-(2,5-dihydroxyphenyl) [OH, OH] | b | 2 HCl | 178-179 (decomp.) |
| 62 | -N(piperazinyl)-N-CH₂-CH(OH)-CH₂-O-NH₂ | b | 4 HCl | 188-190 (decomp.) |
| 63 | -N(1,2,4-triazolyl) | b | 2 HCl | 108-109 |
| 64 | theophyllin-7-yl (1,3-dimethylxanthine) | b | cyclohexyl-NH-SO₃H | 153-154 |

TABLE 2-continued

Examples according to formula $$H_2N-O-CH_2-CH(OH)-CH_2-X \quad (I)$$

| Example | X | Process | isolated as | Melting or boiling point (mm Hg) °C. |
|---|---|---|---|---|
| 65 | benzimidazole (N-methyl) | b | 1 HCl cyclamate | 138–140 (decomp) 122–123 |
| 66 | —NHOH | b | 2 HCl | from 54 (decomp.) |

TABLE 3

Further intermediate compounds of formula $$CH_3-C(OC_2H_5)=N-O-CH_2-CH(OH)-CH_2-X$$

| X | Melting or boiling point (mm Hg) in °C. |
|---|---|
| —OH (VIII) | 34 (0.1) |
| —O—C$_6$H$_5$ (IX) | 127–129 (0.07) 41–43 |
| —NH—C$_2$H$_5$ | 66 |
| —N(C$_2$H$_5$)$_2$ | 98 (0.5) |
| —N(C$_4$H$_9$)$_2$ | 142–145 (0.5) |
| —NH—C(CH$_3$)$_3$ | 105–108 (0.2) |
| —N(CH$_2$—CH$_2$—OH)$_2$ | 175–180 (0.5) |
| —NH—CH(CH$_3$)—C(=O)OC$_2$H$_5$ | 148–150 (0.05) |
| —NH—CH(CH$_3$)—CH$_2$—C$_6$H$_5$ | 167–170 (0.05) |
| —N(CH$_3$)—C$_6$H$_5$ | 148 (0.3) |
| —NH—C$_6$H$_4$(o-OCH$_3$) | 173–176 (0.08) |
| —NH—C$_6$H$_4$(m-CF$_3$) | 138–141 (0.01) |
| —NH—C$_6$H$_4$(p-Cl) | 175–178 (0.05) |
| —N(piperidino) | 105 (0.5) |
| —N(hexamethyleneimino) | 130–132 (0.5) |

TABLE 3-continued

Further intermediate compounds of formula

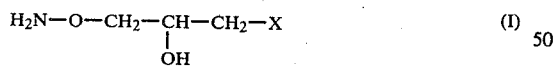

| X | Melting or boiling point (mm Hg) in °C. |
|---|---|
| (2,5-dimethylpyrrolidinyl) | 111–115 (0.5) |
| (2,6-dimethylpiperidinyl) | 138 (0.3) |
| (2,2,6,6-tetramethylpiperidinyl) | 134–136 (0.5) |
| (4-(2-hydroxyethyl)piperazinyl) | 165 (0.2) |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A compound of Formula I:

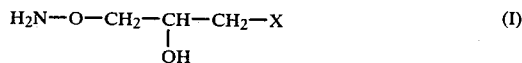

wherein X is piperazine substituted in a 4-position by a member selected from the group consisting of:
 (a) alkyl and hydroxyalkyl having up to four carbon atoms; and
 (b) phenylalkyl and diphenylalkyl having up to four carbon atoms in the alkyl moiety wherein the phenyl radicals are unsubstituted or are substituted by halogen; and
 (c) 3-aminooxy-2-hydroxypropyl.

2. A compound of Formula I:

$$H_2N-O-CH_2-CH(OH)-CH_2-X \quad (I)$$

wherein X is piperazinyl substituted in 4-position by a member selected from the group consisting of:
 (a) methyl;
 (b) hydroxyethyl;
 (c) benzyl;
 (d) diphenylmethyl;
 (e) (fluorophenyl)(phenyl)methyl;
 (f) phenyl;
 (g) dimethylphenyl;
 (h) methoxyphenyl;
 (i) ethoxyphenyl;
 (j) trifluoromethylphenyl;
 (k) chlorophenyl;
 (l) hydroxyphenyl;
 (m) dihydroxyphenyl; and
 (n) (3-aminooxy-2-hydroxy)propyl.

3. A compound of Formula I:

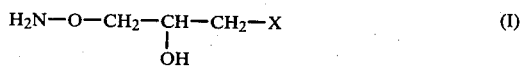

wherein X is a member selected from the group consisting of 4-phenyl-piperazinyl, and 4-phenyl-piperazinyl substituted by methyl, methoxy, ethoxy, trifluoromethyl, chloro, and hydroxy.

4. A compound of claim 3 of the formula:

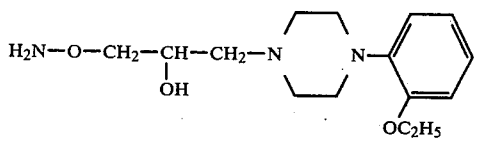

5. A compound of claim 3 of the formula:

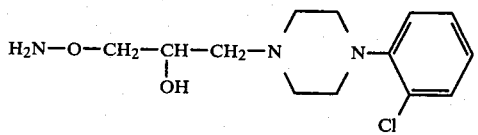

6. A compound of the formula:

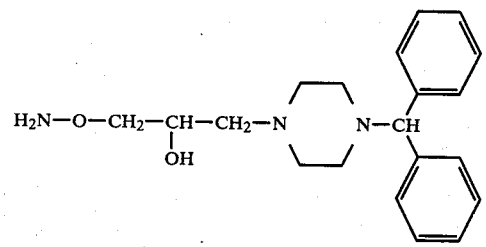

* * * * *

UNITED STATES PATENT OFFICE
CERTIFICATE OF CORRECTION

Patent No. 4,404,384      Dated September 13, 1983

Inventor(s) GEBERT et al

It is certified that error appears in the above-identified patent and that said Letters Patent are hereby corrected as shown below:

On the title page at item [30], for "1977"
    read --1976--

*Signed and Sealed this*

*Twentieth* Day of *March 1984*

[SEAL]

*Attest:*

GERALD J. MOSSINGHOFF

*Attesting Officer*      *Commissioner of Patents and Trademarks*